United States Patent [19]

Lowey

[11] 4,259,314

[45] Mar. 31, 1981

[54] METHOD AND COMPOSITION FOR THE PREPARATION OF CONTROLLED LONG-ACTING PHARMACEUTICALS

[76] Inventor: Hans Lowey, 7 Deerfield La., Mamaroneck, N.Y. 10543

[21] Appl. No.: 102,227

[22] Filed: Dec. 10, 1979

[51] Int. Cl.³ .................. A61K 9/02; A61K 9/20; A61K 9/22; A61K 47/00
[52] U.S. Cl. .................. 424/19; 424/22; 424/362
[58] Field of Search .................. 424/19–22, 424/362

[56] References Cited

U.S. PATENT DOCUMENTS

| | | | |
|---|---|---|---|
| 3,424,842 | 1/1969 | Nurnberg | 424/94 |
| 3,776,001 | 12/1973 | Hanke et al. | 128/271 |
| 3,845,201 | 10/1974 | Haddad et al. | 424/19 |
| 3,868,445 | 2/1975 | Ryde et al. | 424/14 |
| 3,870,790 | 3/1975 | Lowey et al. | 424/19 |
| 3,875,300 | 4/1975 | Homm et al. | 424/28 |
| 4,179,497 | 12/1979 | Cohen et al. | 424/22 |

FOREIGN PATENT DOCUMENTS 1018456 10/1977 Canada.
2718260 11/1977 Fed. Rep. of Germany.
1171691 11/1969 United Kingdom.

OTHER PUBLICATIONS

Forest Laboratories, Inc., Lowey H. Tablets Based on Hydroxy-Propyl Methyl Cellulose Treated by Adjusting Moisture Content to 85% Then Drying to 5% for Continuous Release of Pharmaceutical DT2718260 (11-17-77) FR2358895, J52145514.
Lowey, H. Slow Release Compns. Based on Hydroxypropylmethyl Cellulose, NL7308859, DT2332484, FR290409, GB1430684, CA1018456, J4905419.
Hercules, Inc., "Fact Sheet On Klucel", 2 pp. Dec. 4, 1972.
Hercules, Inc., "Klucel Hydroxypropyl Cellulose", 32 pp. (1971).
Klug, J. Polymer. Sci., Part C, No. 36:491–508 (1971) "Some Properties of Water-Soluble Hydroxyalkyl Celluloses and Their Derivatives".

*Primary Examiner*—Shep K. Rose
*Attorney, Agent, or Firm*—Lewis H. Eslinger

[57] ABSTRACT

A method and composition for the preparation of controlled long-acting pharmaceuticals using a dry carrier or base material comprising an effective amount of hydroxypropyl methylcellulose and hydroxypropyl cellulose suitable for use with both hygroscopic and non-hygroscopic materials. The controlled long-acting products of the invention are suitable for use in the form of lozenges, buccal tablets, oral tablets or suppositories.

28 Claims, No Drawings

METHOD AND COMPOSITION FOR THE PREPARATION OF CONTROLLED LONG-ACTING PHARMACEUTICALS

This invention relates to a new controlled long-acting dry pharmaceutical composition using a dry carrier or base material in admixture with an effective amount of a therapeutic agent or medicament. The sustained release products in the form of lozenges, buccal tablets, oral tablets or suppositories prepared in accordance with the present invention can be used for both conventional applications and applications which were not heretofore possible. The invention is in a dry carrier which can be admixed with a hygroscopic therapeutic agent to produce an effective dry pharmaceutical composition. The dry carrier can be used equally well with both non-hygroscopic and hygroscopic materials.

BACKGROUND OF THE INVENTION

The advantages of long-acting or sustained release products are well-known to the art and are of extreme importance in the pharmaceutical field. Through the use of such products, medication can be administered for uniform and continuous release over a prolonged period of time to achieve a stable and desired blood level of the active ingredient without requiring frequent administration of the medicament. Numerous objectives must be considered in the preparation of an effective controlled release pharmaceutical formulation. Among such objectives are obtaining uniform and constant dissolution and efficacy for a prolonged period of time, ease of preparation, acceptability of taste and adaptability for use with a wide variety of therapeutic agents.

Previously developed long-acting formulations are only capable of satisfying some of these objectives. For example, some conventional sustained release therapeutic compositions use a base material comprised of a copolymer of cellulose material in admixture with an active therapeutic ingredient. The copolymer used is difficult to manufacture and has a moisture content which renders it unacceptable for use with hygroscopic materials. The moisture content of the heretofore known copolymer base materials, for example, results in the production of salicylic acid when aspirin contacts the copolymer. The salicylic acid so produced exhibits undesirable taste and odor and is not permitted to be marketed in this form. Therefore, it is desirable to develop a dry pharmaceutical carrier which can be effectively used with hygroscopic active therapeutic agents such as aspirin. From the standpoint of maximizing the effectiveness and adaptability of a carrier for use with both non-hygroscopic and hygroscopic materials, a new dry carrier composition with a minimum moisture content is especially important.

The use of cellulosic derivatives such as hydroxypropyl methylcellulose as an ingredient in pharmaceutical formulations is known. However, none of these formulations has been found to be effective in admixture with hygroscopic therapeutic agents. Thus, in U.S. Pat. No. 3,590,117 the inadequacy of hydroxypropyl methylcellulose for use in long-lasting troches used as a vehicle for administering active medicaments is disclosed. The use of high viscosity gums such as hydroxypropyl methylcellulose having a viscosity of 15,000 centipoise for a 2% aqueous solution at 20° C. proved unacceptable because the troche would "flake-off" in the mouth rather than dissolve uniformly. Alternatively, troches made from low viscosity hydroxypropyl methylcellulose, while avoiding the problem of "flaking-off", produced a "gagging" effect due to the highly viscous and adhesive characteristics of the saliva produced in the mouth. Later developments, as described in U.S. Pat. No. 3,870,790, relate to mixing an active therapeutic ingredient with a copolymer of a premoisturized hydroxypropyl methylcellulose powder which could also be optionally mixed with an ethylcellulose powder. The release period of the active medicament is controlled as a function of a predetermined moisture content of the alkylated cellulose carrier powder; however, the pharmaceutical formulations containing such a moisturized copolymer could not be successfully used with hygroscopic materials.

Therefore, a need exists for a controlled long-acting dry pharmaceutical formulation which can be easily and inexpensively prepared and which has all of the desirable properties of uniform and continuous dissolution over a prolonged period of time and which can also be used with a greater variety of medicaments including those which are hygroscopic.

OBJECTS OF THE INVENTION

It is accordingly an object of the invention to provide a controlled, long-acting pharmaceutical composition which can be effectively used with both hygroscopic and non-hygroscopic therapeutic agents.

It is another object of the invention to provide a new base material consisting of a dry carrier which can be used in admixture with hygroscopic therapeutic agents and which can also be easily and inexpensively manufactured.

It is a further object to provide a method for producing a controlled, long-acting dry pharmaceutical composition incorporating a new dry carrier.

It is still a further object of the invention to provide a method and composition for preparing a sustained release dry pharmaceutical formulation which can be administered in the form of a lozenge, buccal tablet, oral tablet or suppository.

Other objects of the invention will be apparent from the following discussion.

GENERAL DESCRIPTION

These objects are achieved by using a dry carrier prepared by mixing a major proportion of hydroxypropyl methylcellulose with a minor proportion of hydroxypropyl cellulose. For purposes of the following description all percentages of dry carrier are based on a water-free composition. All reference hereinafter to water content, is also based on the water-free composition of the dry carrier. The carrier is dried to a moisture content of less than 1%. The dry carrier so obtained is then combined with a therapeutically effective amount of an active medicament and, if desired, a suitable lubricant to form a dry pharmaceutical composition. Skim milk can also be added to the dry carrier to further improve its effectiveness. This formulation is then shaped and compressed into a suitable form adapted to be retained in the mouth for buccal or sublingual administration, to be swallowed for absorption in the gastrointestinal tract or to be applied as a suppository. The dry carrier so obtained can be effectively used with both non-hygroscopic and hygroscopic therapeutic agents.

In a preferred embodiment of the invention, a controlled release dry pharmaceutical composition is prepared with a dry carrier comprised of 80 to 95% of hydroxypropyl methylcellulose and 20 to 5% of hydroxypropyl cellulose. The carrier is dried to a moisture content of not more than 1%. To further increase the effectiveness of the dry carrier, when used with hygroscopic materials, the moisture content should not exceed ½%.

In a particularly preferred embodiment of the invention, hydroxypropyl methylcellulose having a viscosity in the range of 50 to 4000 centipoise for a 2% aqueous solution at 20° C. is used. It is also advantageous to use hydroxypropyl cellulose having a viscosity in the range of 1500 to 2500 centipoise for a 1% aqueous solution or 4000 to 6500 centipoise for a 2% aqueous solution at 25° C.

It is most preferred to prepare a controlled, long-acting dry pharmaceutical composition containing a dry carrier comprised of 40 to 70% of hydroxypropyl methylcellulose having a viscosity of about 50 centipoise for a 2% aqueous solution at 20° C., 40 to 20% of hydroxypropyl methylcellulose having a viscosity of about 4000 centipoise for a 2% aqueous solution at 20° C. and 20 to 5% of hydroxypropyl cellulose.

Hydroxypropyl methylcellulose properties having viscosities of 50 and 4000 centipoise for 2% aqueous solutions at 20° C. are known and commercially available as Methocel E-50 and E-4M, respectively (Dow Chemical Company registered trademarks). Hydroxypropyl cellulose as used in accordance with the invention is known and commercially available as Klucel (a Hercules Inc. registered trademark). Hydroxypropyl methylcellulose preparations having viscosities in the range of 50 to 4000 centipoise are combined with hydroxypropyl cellulose to form the dry carrier.

The hydroxypropyl methylcellulose and hydroxypropyl cellulose components are preferably stored prior to use for at least 24 hours under a constant relative humidity of not more than about 40%. After mixing these two components in accordance with the method of the invention and adding the active ingredient, the dry pharmaceutical composition can be compressed and shaped into a convenient solid pharmaceutical form. Depending upon the conditions under which the material is compressed as well as the relative proportions of hydroxypropyl methylcellulose and hydroxypropyl cellulose used, the period of uniform and continuous release of the active ingredient can be pre-determined and varied.

If the pharmaceutical composition is compressed under low pressure, a troche can be prepared capable of being sucked or used in the mouth. A controlled release of the active therapeutic agent, which is mucosally absorbed into the blood stream is achieved. If higher pressures are used to compress the pharmaceutical material a harder and longer-lasting pharmaceutical composition can be prepared suitable for rectal or vaginal application or suitable for swallowing in the form of a tablet. The final products may additionally contain adjuvants such as coloring agents, flavoring agents, synthetic sweetening agents and preservatives.

The pharmaceutical compositions obtained using the dry carrier base material of the invention have controlled, long-acting capability so that therapeutically active agents can be uniformly and continuously released over prolonged periods of time ranging from about 1 to 8, or more, hours. The duration, uniformity and continuity of release of the therapeutically active ingredient can be suitably controlled by varying the relative amounts of hydroxypropyl methylcellulose and hydroxypropyl cellulose and/or by changing the surface of the finished product. The dry pharmaceutical formulation of the invention has considerable flexibility and versatility depending upon the form in which it is administered and the particular nature of the active therapeutic agent combined with the dry carrier base material.

SPECIFIC DESCRIPTION

Following is an illustrative method of preparing a dry pharmaceutical composition of the invention. The hydroxypropyl methylcellulose component identified as Methocel E-50 has the following chemical structure:

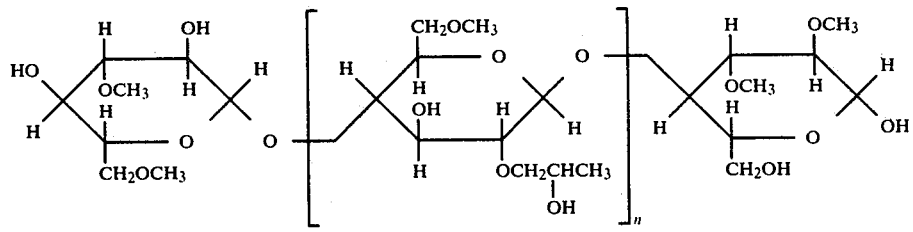

The hydroxypropyl cellulose component identified as Klucel has the following chemical structure:

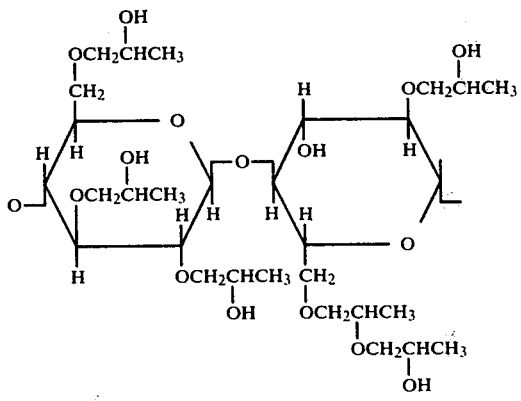

All raw materials including the hydroxypropyl methylcellulose and hydroxypropyl cellulose are stored and exposed to a controlled relative humidity of not more than 40% for at least 24 hours. The hydroxypropyl methylcellulose components with different viscosities are mixed for about one-half hour after which the hydroxypropyl cellulose is added and mixed for about fifteen minutes. The mixture is then dried to a moisture content of not more than 1% to yield a dry carrier base material. The mixture so obtained can be advantageously stored in a double-lined polyethylene bag if not immediately used.

After the dry carrier is prepared, any desired active therapeutic ingredient and lubricant can be admixed in a known and conventional manner to produce a pharmaceutically active composition. This final mixture is then compressed, preferably at about 40% humidity, to yield a suitable dry pharmaceutical formulation which can be packed or stored at normal room temperature.

The dry carrier prepared in accordance with the present invention can be used with a wide variety of active therapeutic agents of which a few are described in the specific illustrative examples which follow:

EXAMPLE 1: BUCCAL TABLETS

| No. | Component | Grams |
|---|---|---|
| 1. | Nitroglycerin with Lactose (1:9) | 50 |
| 2. | Hydroxypropylmethylcellulose E-50 | 40 |
| 3. | Hydroxypropylmethylcellulose E-4M | 25 |
| 4. | Hydroxypropylcellulose | 5 |
| 5. | Stearic Acid (triple pressed) | 1 |
| 6. | Lactose U.S.P. anh. spray dried | 47.5 |

The compositions of Examples 2 through 13 are tablets for oral administration:

EXAMPLE 2

| No. | Component | Grams |
|---|---|---|
| 1 | Nitroglycerin with Lactose (1:9) | 28.6 |
| 2. | Hydroxypropylmethylcellulose E-50 | 200 |
| 3. | Hydroxypropylmethylcellulose E-4M | 75 |
| 4. | Hydroxypropylcellulose | 25 |
| 5. | Magnesium Stearate | 1.5 |
| 6. | Syloid 244 | 2.5 |
| 7. | Stearic Acid | 2.5 |

EXAMPLE 3

| No. | Component | Grams |
|---|---|---|
| 1. | Theophyllin | 105 |
| 2. | Hydroxypropylmethylcellulose E-50 | 200 |
| 3. | Hydroxypropylmethylcellulose E-4M | 60 |
| 4. | Hydroxypropylcellulose | 15 |
| 5. | Stearic Acid | 6. |
| 6. | Magnesium Stearate | 6. |
| 7. | Syloid 244 | 3. |

EXAMPLE 4

| No. | Component | Grams |
|---|---|---|
| 1. | Quinidine Gluconate | 324. |
| 2. | Corn Starch U.S.P. | 152. |
| 3. | Acacia U.S.P. | 136. |
| 4. | Hydroxypropylmethylcellulose E-50 | 225 |
| 5. | Hydroxypropylmethylcellulose E-4M | 30 |
| 6. | Hydroxypropylcellulose | 20 |
| 7. | Carbowax 6000 W | 7. |

-continued

| No. | Component | Grams |
|---|---|---|
| 8. | Cherry Flavor | 16. |

EXAMPLE 5

| No. | Component | Grams |
|---|---|---|
| 1. | Oxytetracycline Dihydrate | 162.5 |
| 2. | Hydroxypropylmethylcellulose E-50 | 110 |
| 3. | Hydroxypropylmethylcellulose E-4M | 70 |
| 4. | Hydroxypropylcellulose | 20 |
| 5. | Syloid | 4. |
| 6. | Stearic Acid | 7. |

EXAMPLE 6

| No. | Component | Grams |
|---|---|---|
| 1. | Nitrofurantoin | 100. |
| 2. | Hydroxypropylmethylcellulose E-50 | 125 |
| 3. | Hydroxypropylmethylcellulose E-4M | 100 |
| 4. | Hydroxypropylcellulose | 25 |
| 5. | Syloid | 1. |
| 6. | Stearic Acid | 5. |

EXAMPLE 7

| No. | Component | Grams |
|---|---|---|
| 1. | Aminophyllin | 300. |
| 2. | Hydroxypropylmethylcellulose E-50 | 80 |
| 3. | Hydroxypropylmethylcellulose E-4M | 50 |
| 4. | Hydroxypropylcellulose | 20 |
| 5. | Syloid | 3. |
| 6. | Stearic Acid | 7. |

EXAMPLE 8

| No. | Component | Grams |
|---|---|---|
| 1. | Ascorbic Acid | 100. |
| 2. | Hydroxypropylmethylcellulose E-50 | 40 |
| 3. | Hydroxypropylmethylcellulose E-4M | 25 |
| 4. | Hydroxypropylcellulose | 10 |
| 5. | Stearic Acid | 1. |
| 6. | Syloid | 2. |

EXAMPLE 9

| No. | Component | Grams |
|---|---|---|
| 1. | Aspirin U.S.P.* | 500. |
| 2. | Hydroxypropylmethylcellulose E-50 | 225 |
| 3. | Hydroxypropylmethylcellulose E-4M | 30 |
| 4. | Hydroxypropylcellulose | 20 |
| 5. | Glycine | 45. |
| 6. | Syloid | 4.5 |

EXAMPLE 10

| No. | Component | Grams |
|---|---|---|
| 1. | Magnesium hydroxide | 486. |
| 2. | Hydroxypropylmethylcellulose E-50 | 225. |
| 3. | Hydroxypropylmethylcellulose E-4M | 60. |
| 4. | Hydroxypropylcellulose | 15. |
| 5. | Gum Acacia | 10. |
| 6. | Syloid 244 | 5. |
| 7. | Stearic Acid | 10. |

EXAMPLE 11

| No. | Component | Grams |
|---|---|---|
| 1. | Dihydroergotamine Methane Sulfonate | 2.50 |
| 2. | Butylhydroxyanisol | 1.25 |
| 3. | Hydroxypropylmethylcellulose E-50 | 120. |
| 4. | Hydroxypropylmethylcellulose E-4M | 120. |
| 5. | Hydroxypropylcellulose | 60. |
| 6. | Syloid 244 | 2. |
| 7. | Stearic Acid | 4. |

EXAMPLE 12

| No. | Component | Grams |
|---|---|---|
| 1. | Dexamethasone | 2.34 |
| 2. | Hydroxypropylmethylcellulose E-50 | 125. |
| 3. | Hydroxypropylmethylcellulose E-4M | 100. |
| 4. | Hydroxypropylcellulose | 25. |
| 5. | Syloid 244 | 3. |
| 6. | Stearic Acid | 6. |

EXAMPLE 13

| No. | Component | Grams |
|---|---|---|
| 1. | Potassium Chloride | 250. |
| 2. | Hydroxypropylmethylcellulose E-50 | 240. |
| 3. | Hydroxypropylmethylcellulose E-4M | 80. |
| 4. | Hydroxypropylcellulose | 80. |
| 5. | Carbowax 6000 W | 10. |
| 6. | Syloid 244 | 10. |

EXAMPLE 14: LOZENGES

| No. | Component | Grams |
|---|---|---|
| 1. | Prednisolone | 15.75 |
| 2. | Hydroxypropylmethylcellulose E-50 | 85 |
| 3. | Hydroxymethylpropylcellulose E-4M | 65 |
| 4. | Hydroxypropylcellulose | 25 |
| 5. | Syloid | 1. |
| 6. | Stearic Acid | 2.5 |

EXAMPLE 15: LOZENGES

| No. | Component | Grams |
|---|---|---|
| 1. | Dextrometorphan | 25. |
| 2. | Hydroxypropylmethylcellulose E-50 | 85 |
| 3. | Hydroxypropylmethylcellulose E-4M | 65 |
| 4. | Hydroxypropylcellulose | 25 |
| 5. | Powdered skimmed milk | 25. |

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

I claim:

1. A method for preparing a controlled long-acting release dry pharmaceutical formulation containing a therapeutic agent and a dry carrier comprising the steps of:
   (a) forming a dry carrier comprising 80 to 95%, of said dry carrier, of hydroxypropyl methylcellulose and 20 to 5% of hydroxopropyl cellulose,
   (b) drying said carrier to a moisture content of not more than 1%,
   (c) mixing the dry carrier with a therapeutically effective amount of a therapeutic agent to form the dry pharmaceutical formulation, and
   (d) compressing said dry pharmaceutical formulation into a suitable form.

2. The method of claim 1 wherein the dry carrier includes hydroxypropyl methylcellulose having a viscosity in the range of 50 to 4000 centipoise for a 2% aqueous solution at 20° C.

3. The method of claim 2 wherein the dry carrier includes hydroxypropyl cellulose having a viscosity in the range of 1500 to 2500 centipoise for a 1% aqueous solution at 25° C. or 4000 to 6500 centipoise for a 2% aqueous solution at 25° C.

4. The method of claim 1 wherein the dry carrier includes 40 to 75% of hydroxypropyl methylcellulose having a viscosity of about 50 centipoise for a 2% aqueous solution at 20° C. and 40 to 20% hydroxypropyl methylcellulose having a viscosity of about 4000 centipoise for a 2% aqueous solution at 20° C. and 20 to 5% of hydroxypropyl cellulose.

5. The method of claim 1 or 4 wherein the dry carrier is dried to a moisture content of not more than 0.5%.

6. The method of claim 1 or 4 wherein the hydroxypropyl methylcellulose and hydroxypropyl cellulose are exposed to a humidity of not more than 40% for at least 24 hours.

7. The method of claim 1 wherein the dry pharmaceutical formulation is in the form of either lozenges, buccal tablets, oral tablets or suppositories.

8. A method for preparing a dry carrier comprising the steps of:
   (a) mixing 80 to 95% of hydroxypropyl methylcellulose and 20 to 5% of hydroxypropyl cellulose, and
   (b) drying said carrier to a moisture content of not more than 1%.

9. The method of claim 8 wherein the dry carrier includes hydroxypropyl methylcellulose having a viscosity in the range of 50 to 4000 centipoise for a 2% aqueous solution at 20° C.

10. The method of claim 9 wherein the dry carrier includes hydroxypropyl cellulose having a viscosity in the range of 1500 to 2500 centipoise for a 1% aqueous solution at 25° C. or 4000 to 6500 centipoise for a 2% aqueous solution at 25° C.

11. The method of claim 8 wherein the dry carrier includes 40 to 75% of hydroxypropyl methylcellulose having a viscosity of about 50 centipoise for a 2% aqueous solution at 20° C. and 40 to 20% hydroxypropyl methylcellulose with a viscosity of about 4000 centipoise for a 2% aqueous solution at 20° C. and 20 to 5% of hydroxypropyl cellulose.

12. The method of claim 8 or 11 wherein the dry carrier is dried to a moisture content of not more than 0.5%.

13. The method of claim 8 or 11 wherein the hydroxypropyl methylcellulose and hydroxypropyl cellulose are exposed to a humidity of not more than 40% for at least 24 hours.

14. A sustained release dry pharmaceutical formulation which comprises:
 (a) a dry carrier comprising 80 to 95% of hydroxypropyl methylcellulose and 20 to 5% of hydroxypropyl cellulose, said carrier containing not more than 1% moisture, and
 (b) up to 600 mg of an active therapeutic agent.

15. The pharmaceutical formulation of claim 14 wherein up to 1200 mg of the active therapeutic agent is used for suppositories.

16. The pharmaceutical formulation of claim 14 further comprising an effective amount of a pharmaceutically suitable lubricant.

17. The pharmaceutical formulation of claim 14 wherein the dry carrier is comprised of hydroxypropyl methylcellulose with a viscosity in the range of 50 to 4000 centipoise for a 1% aqueous solution at 20° C.

18. The pharmaceutical formulation of claim 17 wherein the dry carrier includes hydroxypropyl cellulose having a viscosity in the range of 1500 to 2500 centipoise for a 1% aqueous solution at 25° C. or 4000 to 6500 centipoise for a 2% aqueous solution at 25° C.

19. The pharmaceutical formulation of claim 14 wherein the dry carrier includes 40 to 75% of hydroxypropyl methylcellulose having a viscosity of about 50 centipoise for a 2% aqueous solution at 20° C. and 40 to 20% hydroxypropyl methylcellulose with a viscosity of about 4000 centipoise for a 2% aqueous solution at 20° C. and 20 to 5% of hydroxypropyl cellulose.

20. The pharmaceutical formulation of claim 14 or 19 wherein the dry carrier has a moisture content of not more than 0.5%.

21. The pharmaceutical formulation of claim 14 or 19 wherein the hydroxypropyl methylcellulose and hydroxypropyl cellulose are exposed to a humidity of not more than 40% for at least 24 hours.

22. The pharmaceutical formulation of claim 14 or 19 wherein said formulation is in the form of either lozenges, buccal tablets, oral tablets or suppositories.

23. A dry carrier material comprising 80 to 95% of hydroxypropyl methylcellulose and 20 to 5% of hydroxypropyl cellulose wherein said carrier contains not more than 1% moisture.

24. The dry carrier of claim 23 includes hydroxypropyl methylcellulose having a viscosity in the range of 50 to 4000 centipoise for a 2% aqueous solution at 20° C.

25. The dry carrier of claim 24 wherein said carrier includes hydroxypropyl cellulose having a viscosity in the range of 1500 to 2500 centipoise for a 1% aqueous solution at 25° C. or 4000 to 6500 centipoise for a 2% aqueous solution at 25° C.

26. The dry carrier of claim 23 wherein said carrier includes 40 to 75% of hydroxypropyl methylcellulose having a viscosity of about 50 centipoise for a 2% aqueous solution at 20° C. and 40 to 20% hydroxypropyl methylcellulose with a viscosity of about 4000 centipoise for a 2% aqueous solution at 20° C. and 20 to 5% of hydroxypropyl cellulose.

27. The dry carrier of claim 23 or 26 wherein the total moisture content is less than 0.5%.

28. The dry carrier of claim 23 or 26 wherein the hydroxypropyl methylcellulose and hydroxypropyl cellulose are exposed to a humidity of not more than 40% for at least 24 hours.

* * * * *